(12) United States Patent
Kamal et al.

(10) Patent No.: US 6,683,073 B1
(45) Date of Patent: Jan. 27, 2004

(54) PYRIMIDINE LINKED PYRROLO[2,1-C][1,4] BENZODIAZEPINES AS POTENTIAL ANTITUMOUR AGENTS

(75) Inventors: Ahmed Kamal, Hyderabad (IN); Karnati Laxma Reddy, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,103

(22) Filed: Mar. 25, 2003

(51) Int. Cl.[7] .................. C07D 487/00; A61K 31/55
(52) U.S. Cl. .................. 514/212.05; 540/496
(58) Field of Search .................. 540/496; 514/212.05

(56) References Cited

PUBLICATIONS

Thurston et al. (J. Org. Chem. 1996, 61, 8141–8147).*

* cited by examiner

Primary Examiner—Bruck Kifle

(74) Attorney, Agent, or Firm—Ladas & Parry

(57) ABSTRACT

The present invention relates to a process for the preparation of novel pyrrolo [2,1-c][1,4]benzodiazepines useful as potential antitumour agents. This invention also relates to a process for the preparation of new pyrrolo[2,1-c][1,4] benzodiazepines as potential antitumour agents. More particularly, it provides a process for the preparation of 7-methoxy-8-[6'-(4"-fluorophenyl)-2'-methylpyrimidine-4'-yloxy]alkoxy-(11aS)-1,2,3,11a-tetrahydro-5H-pyrrolo[2,1,c][1,4]benzodiazepin-5-one with aliphatic chain length variations for the compounds and it also describes the anticancer (antitumour) activity. The structural formula of novel pyrrolo[2,1-c][1,4]benzodiazepine is as follows.

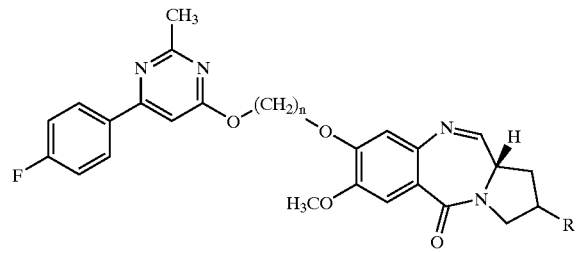

15 Claims, No Drawings

PYRIMIDINE LINKED PYRROLO[2,1-C][1,4] BENZODIAZEPINES AS POTENTIAL ANTITUMOUR AGENTS

FIELD OF THE INVENTION

The present invention relates to a process for the preparation of novel pyrimidine linked pyrrolo [2,1-c][1,4] benzodiazepines useful as potential antitumour agents. This invention also relates to a process for the preparation of new pyrimidine linked pyrrolo[2,1-c][1,4]benzodiazepines as potential antitumour agents. More particularly, it provides a process for the preparation of 7-methoxy-8-[6'-(4"-fluorophenyl)-2'-methylpyrimidine-4'-yloxy]alkoxy-(11aS)-1,2,3,11a-tetrahydro-5H-pyrrolo[2,1,c][1,4]benzodiazepin-5-one with aliphatic chain length variations for the compounds and it also describes the anticancer (antitumour) activity. The structural formula of novel pyrrolo[2,1-c][1,4] benzodiazepine is as follows.

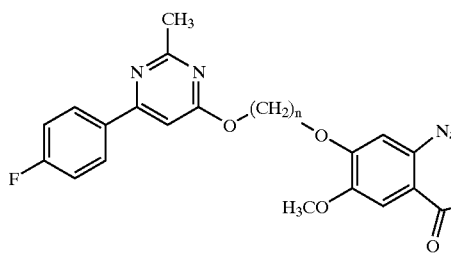

BACKGROUND OF THE INVENTION

Pyrrolo[2,1-c][1,4]benzodiazepines anti-tumour antibiotics are commonly known as anthramycin class of compounds. In the last few years, a growing interest has been shown in the development of new pyrrolo[2,1-c][1,4] benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochmestry*, 1981, 20, 7572). The molecules have a right-handed twist, which allows them to follow the curvature of the minor groove of B-form double-stranded DNA spanning three base pairs. Recently, PBD dimers have been developed that comprises two C2-exo-methylene-substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.*, 1996, 61, 8141–8147). Recently, a non-crass—linking—mixed imine-amide PBD dimers have been synthesized which have significant DNA binding ability and potent anti tumour activitiy. (Kamal, A.; Ramesh, G.; Laxman, N.; Ramulu, p.; Srinivas, O.; Neelima, K.; Kumar, K. K.; Srinu, V. B.; Nagarajaram, H. M. *J. Med. Chem.* 2002, 45, 4679).

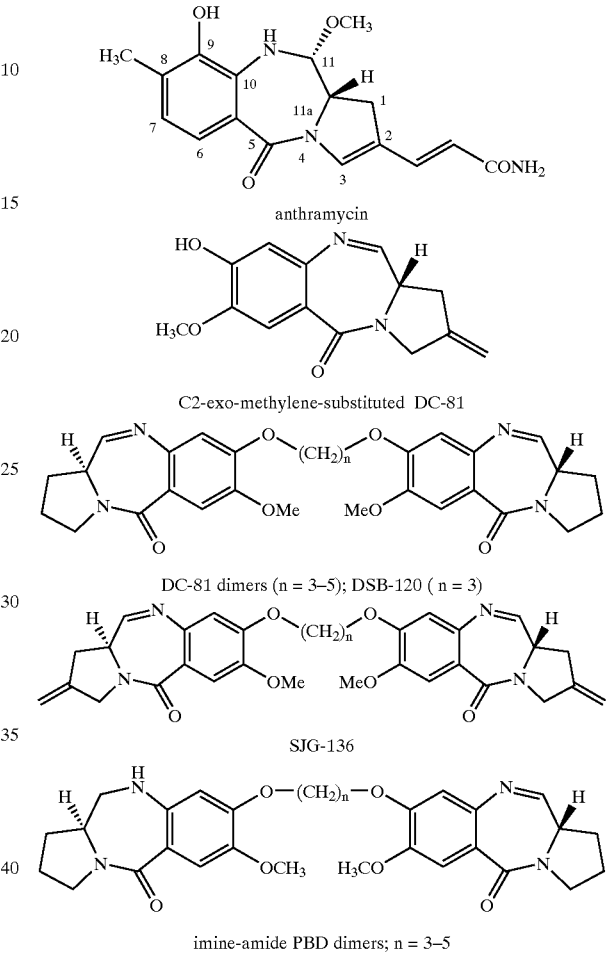

Naturally occurring pyrrolo[2,1-c][1,4]benzodiazepines belong to a group of antitumour antibiotics derived from Streptomyces species. Recently, there is much impetus for the PBD systems as they can recognize and bind to specific sequence of DNA. Examples of naturally occurring PBD's include anthramycin, DC-81, tomaymycin, sibiromycin and neothramycin. However, the clinical efficacy for these antibiotics is hindered by several limitations, such as poor water solubility and cardiotoxicity and development of drug resistance and metabolic inactivation.

OBJECTS OF THE INVENTION

The main object of the present invention is to provide new pyrrolo[2,1-c][1,4]benzodiazepines useful as antitumour agents.

Another object of the present invention is to provide a process for the preparation of novel pyrrolo[2,1-c][1,4] benzodiazepines useful as antitumour agents.

SUMMARY OF THE INVENTION

Accordingly the present invention provides a process for the preparation of a novel pyrrolo[2,1-c][1,4] benzodiazepine of formula VI wherein R=H, OH, OAc and n is 3–5.

FORMULA VI

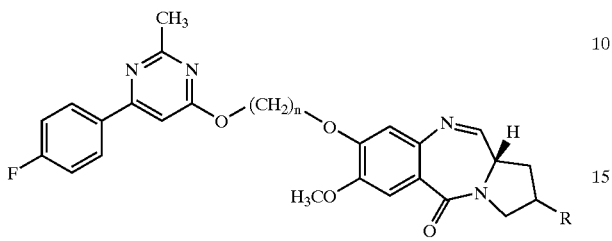

The present invention also provides a process for preparation of pyrrolo[2,1-c][1,4]benzodiazepines of formula VI above wherein R=H, OH, OAc and n is 3 to 5 which comprises reacting 6-4-(4-fluorophenyl)-2-methyl-4-pyrimidinol of formula I with dibromoalkanes in an aprotic water miscible organic solvents like acetone, THF and DMF in presence of mild inorganic bases like $K_2CO_3$, $CsCO_3$ and $BaCO_3$ upto refluxing temperature for a period up to 48 h, isolating n-bromoalkyl-6-(4-flurophenyl)-2-methyl-4-pyrimidinyl ether of formula II with (2S)-N-(4-hydroxy-5-methoxy-2-nitrobenzoyl)pyrrolidine-2-carboxaldehyde diethyl thioacetal of formula III in presence of mild inorganic bases like $K_2CO_3$, $CsCO_3$, and $BaCO_3$ in presence of aprotic water miscible organic solvents up to refluxing for a period of 48 h isolating (2S)-N-[{4-[6"-(4'-fluorophenyl)-2'-methylpyrimidine-4'-yloxy]alkoxy}-5-methoxy-2-nitrobenzoyl]pyrrolidine-2-carboxaldehyde diethyl thioacetal IV where n is 3 to 5 by conventional methods, reducing the above nitro compounds of formula IV with $SnCl_2.2H_2O$ in presence of organic solvent up to a reflux temperature, isolating the (2S)-N-[{4-[6'-(4"-fluorophenyl)-2'-methylpyrimidine-4'-yloxy]alkoxy}-5-methoxy-2-amonobenzoyl]pyrrolidine-2-carboxaldehyde diethyl thioacetal of formula V where n is 3 to 5 by known methods, reacting the above said amino compound of formula V with known deprotecting agents in a conventional manner to give novel pyrrolo[2,1-c][1,4]benzodiazepines of formula VI wherein n is as stated above.

The precursor, (2S)-N-(4-hydroxy-5-methoxy-2-nitrobenzoyl)pyrrolidine-2-carboxaldehyde diethyl thioacetal of formula I (intermediates of DC-81) is prepared by literature methods (Thurston, D. E.; Murthy, V. S.; Langley, D. R.; Jones, G. B. *Synthesis*, 1990, 81)

DETAILED DESCRIPTION OF THE INVENTION

Some representative compounds of formula VI present invention are given below:

1. 7-methoxy-8-[6'-(4"-fluorophenyl)-2'-methylpyrimidine-4'-yloxy]propoxy-(11aS)-1,2,3,11a-tetrahydro-5H-pyrrolo[2,1,c][1,4]benzodiazepin-5-one.
2. 7-methoxy-8-[6'-(4"-fluorophenyl)-2'-methylpyrimidine-4'-yloxy]butoxy-(11aS)-1,2,3,11a-tetrahydro5H-pyrrolo[2,1,c][1,4]benzodiazepin-5-one.
3. 7-methoxy-8-[6'-(4"-fluorophenyl)-2'-methylpyrimidine-4'-yloxy]pentoxy-(11aS)-1,2,3,11a-tetrahydro-5H-pyrrolo[2,1,c][1,4]benzodiazepin-5-one.
4. 7-methoxy-8-[6'-(4"-fluorophenyl)-2'-methylpyrimidine-4'-yloxy]propoxy-(4R)-hydroxy-(11aS)-1,2,3,11a-tetrahydro-5H-pyrrolo[2,1,c][1,4]benzodiazepin-5-one
5. 7-methoxy-8-[6'-(4"-fluorophenyl)-2'-methylpyrimidine-4'-yloxy]butoxy-(4R)-hydroxy-(11aS)-1,2,3,11a-tetrahydro-5H-pyrrolo[2,1,c][1,4]benzodiazepin-5-one
6. 7-methoxy-8-[6'-(4"-fluorophenyl)-2'-methylpyrimidine-4'-yloxy]pentoxy-(4R)-hydroxy-(11aS)-1,2,3,11a-tetrahydro-5H-pyrrolo[2,1,c][1,4]benzodiazepin-5-one
7. 7-methoxy-8-[6'-(4"-fluorophenyl)-2'-methylpyrimidine-4'-yloxy]propoxy-(4R)-acetyloxy-(11aS)-1,2,3,11a-tetrahydro-5H-pyrrolo[2,1,c][1,4]benzodiazepin-5-one
8. 7-methoxy-8-[6'-(4"-fluorophenyl)-2'-methylpyrimidine-4'-yloxy]butoxy-(4R)-acetyloxy-(11aS)-1,2,3,11a-tetrahydro-5H-pyrrolo[2,1,c][1,4]benzodiazepin-5-one
9. 7-methoxy-8-[6'-(4"-fluorophenyl)-2'-methylpyrimidine-4'-yloxy]pentoxy-(4R)-acetyloxy-(11aS)-1,2,3,11a tetrahydro5H-pyrrolo[2,1,c][1,4]benzodiazepin-5-one.

These new analogues of pyrrolo[2,1-c][1,4] benzodiazepine hybrids linked at C-8 position have shown promising anticancer activity in various cell lines. The molecules synthesized are of immense biological significance with potential sequence selective DNA-binding property. This resulted in design and synthesis of new congeners as illustrated in Scheme-1, which comprise:

1. Ether linkage at C-8 position of DC-81 intermediates with pyrimidine ring moiety.
2. Refluxing the reaction mixture for 24–48 h.
3. Synthesis of C-8 linked PBD antitumour antibiotic hybrid imines.
4. Purification by column chromatography using different solvents like ethyl acetate, hexane, dichloromethane and methanol.

The following examples are given by way of illustration and therefore should not be construed as limiting the scope of invention.

Scheme I

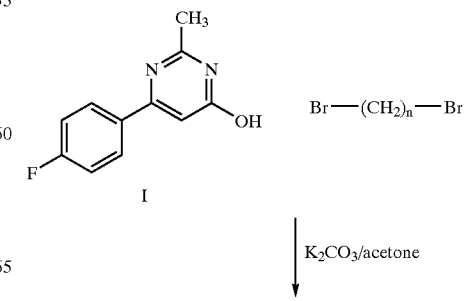

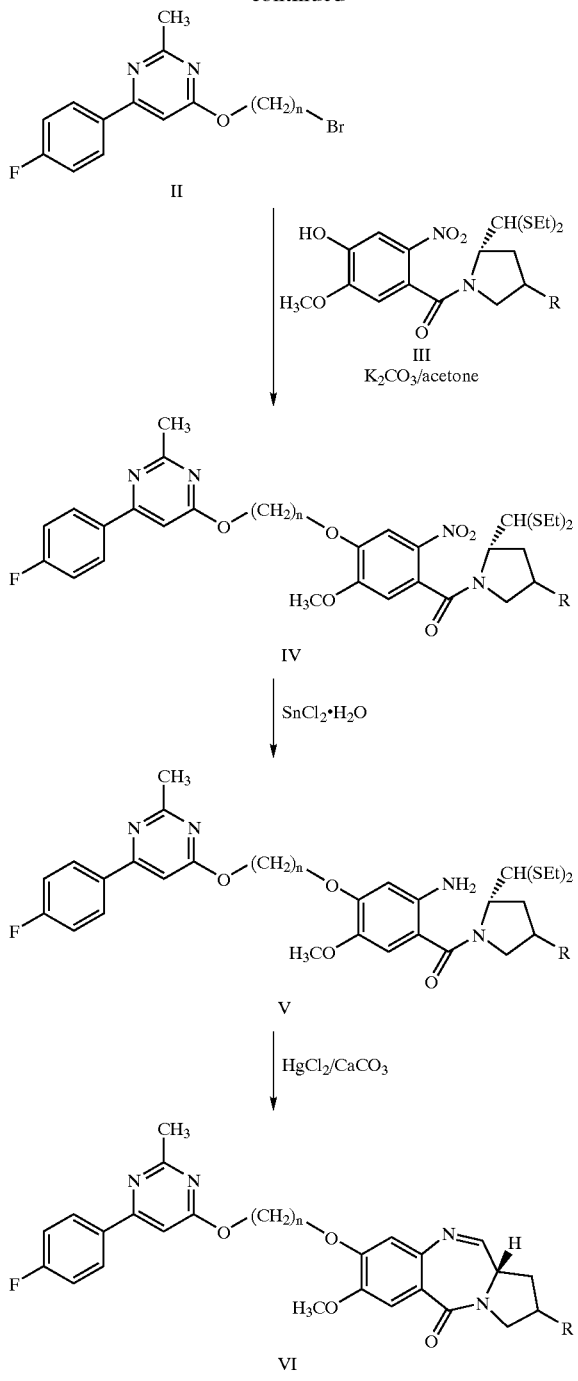

R = H, OH, OAc
n = 3, 4, 5

EXAMPLE 1

Solution of 6-(4-fluorophenyl)-2-methyl-4-pyridinol of formula I (1000 mg 4.90 mmol), 1,3-dibromopropane (2475 mg, 12.25 mmol) and $K_2CO_3$ (2030 mg, 14.7 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II. $^1$H NMR: ($CDCl_3$) 2.1–2.2 (q, 2H), 2.6 (s, 3H), 4.1–4.15 (t, 2H), 4.45–4.55 (t, 2H), 6.6–6.8 (d, 1H), 7.08–7.12 (m, 2H), 8.0 (m, 2H); EIMS 204.

Solution of 3-bromopropyl-6-(4-fluorophenyl)-2-methyl-4-pyrimidyl ether of formula II (1200 mg, 3.69 mmol), A solution of (2S)-N-(4-hydroxy-5-methoxy-2-nitrobenzoyl) pyrrolidine-2-carboxaldehyde diethylthioacetal of formula III (1472 mg, 3.69 mmol) and $K_2CO_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave the pure (2S)-N-[{4-[6'-(4"-fluorophenyl)-2'-methylpyrimidine-4'-yloxy]-propoxy}-5-methoxy-2-nitrobenzoyl]pyrrolidine-2-carboxaldehyde diethyl thioacetal of formula IV. $^1$H NMR: ($CDCl_3$) δ 1.2–1.4 (m, 6H), 1.7–2.42 (m, 6H), 2.65 (s, 3H), 2.65–2.8 (m, 4H), 3.2–3.3 (m, 2H), 3.95 (s, 3H), 4.3 (m, 2H), 4.6 (m, 2H), 4.65–4.8 (m, 1H), 4.85 (d, 1H J=4.2), 6.78 (s, 1H), 6.9 (s, 1H), 7.1–7.2 (m, 2H), 7.7 (s, 1H), 8.0–8.1 (m, 2H); FABMS 939 (M+H)$^+$.

(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal of formula IV (500 mg, 0.78 mmol) was dissolved in methanol (10 mL) and added $SnCl_2.2H_2O$ (873 mg 3.88 mmol) was refluxed for 1.5 h. The reaction mixture was then carefully adjusted to pH 8 with saturated $NaHCO_3$ solution and then extracted with ethyl acetate (3×30 mL). The combined organic phase was dried over $Na_2SO_4$ and evaporated under vacuum to afford the crude (2S)-N-[{4-[6'-(4"-fluorophenyl)-2'-methylpyrimidine-4'-yloxy]propoxy}-5-methoxy-2-aminobenzoyl]pyrrolidine-2-carboxaldehyde diethyl thioacetal of formula V.

A solution of formula V (300 mg, 0.50 mmol), $HgCl_2$ (300 mg, 1.10 mmol) and $CaCO_3$ (120 mg, 1.20 mmol) in $CH_3CN/H_2O$ (3:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]propoxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc-methanol (9:1). $^1$H NMR: ($CDCl_3$) δ 1.9–2.15 (m, 4H), 2.25–2.4 (m, 2H), 2.65 (s, 3H), 3.5–3.8 (m, 3H), 3.95 (s, 1H), 4.0–4.2 (m, 2H), 4.5 (m, 2H), 6.78 (s, 1H), 6.8 (s, 1H), 7.1–7.2 (m, 2H), 7.5 (s, 1H), 7.5 (d, 1H, J=4.3 Hz), 7.95–8.2 (m, 2H); FABMS: 631 (M+H)$^+$.

EXAMPLE 2

A solution of 6-(4-fluorophenyl)-2-methyl-4-pyridinol of formula I (1000 mg 4.90 mmol), 1,4-dibromobutane (2650 mg, 12.25 mmol) and K$_2$CO$_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (4:96) gave the pure 4-bromobutyl-6-(4-fluorophenyl)-2-methyl-4-pyrimidyl ether of formula II. $^1$HNMR: (CDCl$_3$) δ 1.9–2.1 (m, 4H), 2.6–2.7 (s, 3H), 3.45–3.55 (t, 2H), 4.4–4.5 (t, 2H), 6.8 (s, 1H), 7.1–7.2 (m, 2H), 8.0–8.1 (m, 2H); EIMS 204.

Solution of 4-bromobutyl-6-(4-fluorophenyl)-2-methyl-4-pyrimidyl ether of formula II (1300 mg, 3.83 mmol), A solution of (2S)-N-(4-hydroxy-5-methoxy-2-nitrobenzoyl) pyrrolidine-2-carbox-aldehyde diethylthioacetal of formula III (1532 mg, 3.83 mmol) and K$_2$CO$_3$ (1585 mg, 11.47 mmol) in dry acetone (20 ml) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (30:70) gave the pure (2S)-N-[{4-[6'-(4"-fluorophenyl)-2'-methylpyrimidine-4'-yloxy]butoxy)-5-methoxy-2-nitrobenzoyl]pyrrolidine-2-carboxaldehyde diethyl thioacetal of formula IV. $^1$H NMR: (CDCl$_3$) δ 1.9–2.15 (m, 6H), 2.25–2.40 (m, 2H), 2.65 (s, 3H), 3.5–3.8 (m, 3H), 3.95 (s, 1H), 4.0–4.2 (m, 2H), 4.50 (m, 2H), 6.78 (s, 1H), 6.80 (s, 1H), 7.1–7.2 (m, 2H), 7.5 (s, 1H), 7.65 (d, 1H, J=4.4 Hz) 7.95–8.10 (m, 2H); FABMS 939 (M+H)$^+$.

(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal of formula IV (500 mg, 0.76 mmol) was dissolved in methanol (10 mL) and added SnCl$_2$.2H$_2$O (855 mg 3.80 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford the crude (2S)-N-[{4-[6'-(4"-fluorophenyl)-2'-methylpyrimidine-4'-yloxy]butoxy}-5-methoxy-2-aminobenzoyl]pyrrolidine-2-carbox aldehyde diethyl thioacetal of formula V.

Solution of formula V (300 mg, 0.50 mmol), HgCl$_2$ (300 mg, 1.10 mmol) and CaCO$_3$ (120 mg, 1.20 mmol) in CH$_3$CN/H$_2$O (3:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]butoxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc-methanol (97:3). $^1$HNMR (CDCl$_3$) δ 1.92–2.42 (m, 8H), 2.60–2.95 (m, 12H), 3.2–3.88 (m, 6H), 3.92 (s, 6H), 4.14–4.28 (m, 4H), 6.76 (s, 2H), 7.5 (s, 2H), 7.66 (d, 2H); FABMS: 631 (M+H)$^+$.

EXAMPLE 3

Solution of 6-(4-fluorophenyl)-2-methyl-4-pyridinol of formula I (1000 mg 4.90 mmol), 1,5-dibromopentane (2820 mg, 12.25 mmol) and K$_2$CO$_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (3:97) gave the pure 5-bromopentyl-6-(4-fluorophenyl)-2-methyl-4-pyrimidyl ether of formula II. $^1$H NMR: (CDCl$_3$) 1.5–1.6 (q, 2H), 1.7–1.8 (q, 2H), 1.9–2.0 (q, 2H), 2.6 (s, 3H), 3.4 (t, 2H), 4.3–4.4 (t, 3H), 6.7 (s, 1H), 7.1–7.12 (m, 2H), 7.95–8.05 (m, 2H); EIMS 204.

Solution of 5-bromopentyl-6-(4-fluorophenyl)-2-methyl-4-pyrimidyl ether of formula II (1400 mg, 3.97 mmol), A solution of (2S)-N-(4-hydroxy-5-methoxy-2-nitrobenzoyl) pyrrolidine-2-carbox-aldehydediethylthioacetal of formula III (1590 mg, 3.97 mmol) and K$_2$CO$_3$ (1640 mg, 11.898 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (27:73) gave the pure (2S)-N-[{4[6'-(4"-fluorophenyl)-2'-methylpyrimidine-4'-yloxy]pentoxy}-5-methoxy-2▫-nitrobenzoyl]pyrrolidine-2-carboxaldehyde diethyl thioacetal of formula IV. $^1$H NMR (CDCl$_3$) δ 1.2–1.5 (m, 8H), 1.60–2.4 (m, 8H), 2.64 (s, 3H), 2.7–2.82 (m, 4H), 3.2–3.3 (m, 2H), 3.95 (s, 3H), 4.2 (m, 2H), 4.35–4.48 (t, 2H, J=6.5 Hz), 4.62–4.75 (m, H), 4.85 (d, 1H, J=4.2 Hz), 6.78 (s, 1H), 6.82 (s, 1H), 7.05–7.20 (m, 2H), 7.65 (s, 1H), 7.95–8.1 (m, 2H); FABMS 939 (M+H)$^+$.

(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula IV (500 mg, 0.74 mmol) was dissolved in methanol (10 mL) and added SnCl$_2$. 2H$_2$O (840 mg 3.72 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford the crude (2S)-N-[{4-[6'-(4"-fluorophenyl)-2'-methylpyrimidine-4'-yloxy]pentoxy}-5-methoxy-2-aminobenzoyl]pyrrolidine-2-carboxaldehyde diethyl thioacetal of formula V.

Solution of formula V (300 mg, 0.47 mmol), HgCl$_2$ (280 mg, 1.03 mmol) and CaCO$_3$ (110 mg, 1.10 mmol) in CH$_3$CN/H$_2$O (3:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethyl acetate. The filtrate is evaporated in vacuum to get crude 7-methoxy-8-[6'-(4"-fluorophenyl)-2'- methylpyrimidine-4'-yloxy]pentoxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc. $^1$HNMR (CDCl$_3$) δ 1.6–2.2 (m, 10H), 2.65 (s, 3H), 3.6–3.8 (m, 2H), 3.95 (s, 1H), 4.1–4.2 (m, 2H) 4.45 (m, 2H), 6.84 (s, 1H), 6.86 (s, H), 7.1–7.22 (m, 2H), 7.65 (s, 1H), 7.68–7.71 (d, 1H, J=4.4 Hz), 8.0–8.1 (m, 2H); FABMS: 631 (M+H)$^+$.

EXAMPLE 4

Solution of 6-(4-fluorophenyl)-2-methyl-4-pyridinol of formula I (1000 mg 4.90 mmol), 1,3-dibromopropane (2475 mg, 12.25 mmol) and K$_2$CO$_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II.

Solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and K$_2$CO$_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave the pure (4R)-hydroxy-(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal of formula IV.

(4R)-hydroxy-(2S)-N-[{4-[6'-(4"-fluorophenyl)-2'-methylpyrimidine-4'-yloxy]propoxy)-5-methoxy-2-nitrobenzoyl]pyrrolidine-2-carboxaldehyde diethyl thioacetal IV (500 mg, 0.78 mmol) was dissolved in methanol (10 mL) and added SnCl$_2$.2H$_2$O (873 mg 3.88 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford crude (4R)-hydroxy-(2S)-N-[(4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal of formula V.

Solution of formula V (300 mg, 0.5 mmol), HgCl$_2$ (300 mg, 1.10 mmol) and CaCO$_3$ (120 mg, 1.20 mmol) in CH$_3$CN/H$_2$O (3:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]propoxy-(4R)-hydroxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtoAc-methanol (9:1).

EXAMPLE 5

Solution of 6-(4-fluorophenyl)-2-methyl-4-pyridinol of formula I (1000 mg 4.90 mmol), 1,3-dibromopropane (2475 mg, 12.25 mmol) and K$_2$CO$_3$ (2030 mg, 14.7 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II.

Solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and K$_2$CO$_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave the pure (4R)-hydroxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal of formula IV.

(4R)-hydroxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal of formula IV (500 mg, 0.78 mmol) was dissolved in methanol (10 mL) and added SnCl$_2$.2H$_2$O (873 mg 3.88 mmol) was refluxed for 1.5 h. The reaction mixture was then carefully adjusted to pH 8 with saturated NaHCO$_3$ solution and then extracted with ethyl acetate (3×30 mL). The combined organic phase was dried over Na$_2$SO$_4$ and evaporated under vacuum to afford crude (4R)-hydroxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula V.

Solution of formula V (300 mg, 0.5 mmol), HgCl$_2$ (300 mg, 1.10 mmol) and CaCO$_3$ (120 mg, 1.20 mmol) in CH$_3$CN/H$_2$O (3:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethyl acetate. The filtrate was evaporated in vacuum to get crude 7-methoxy-8-[6'-(4"-fluorophenyl)-2'-methylpyrimidine-4'-yloxy]butoxy-(4R)-hydroxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc-methanol (9:1).

EXAMPLE 6

Solution of 6-(4-fluorophenyl)-2-methyl-4-pyridinol of formula I (1000 mg, 4.90 mmol), 1,3-dibromopropane (2475 mg, 12.25 mmol) and $K_2CO_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II.

Solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and $K_2CO_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave pure (4R)-hydroxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula IV.

(4R)-hydroxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula IV (500 mg, 0.78 mmol) was dissolved in methanol (10 mL) and added $SnCl_2.2H_2O$ (873 mg 3.88 mmol) was refluxed for 1.5 h. Reaction mixture was then carefully adjusted to pH 8 with saturated $NaHCO_3$ solution and then extracted with ethyl acetate (3×30 mL). Combined organic phase was dried over $Na_2SO_4$ and evaporated under vacuum to afford crude (4R)-hydroxy-(2S)-N-[{4-[6'-(4"-fluorophenyl)-2'-methylpyrimidine-4'-yloxy]pentoxy}-5-methoxy-2-aminobenzoyl]pyrrolidine-2-carboxaldehyde diethyl thioacetal of formula V.

Solution of formula V (300 mg, 0.50 mmol), $HgCl_2$ (300 mg, 1.10 mmol) and $CaCO_3$ (120 mg, 1.20 mmol) in $CH_3CN/H_2O$ (3:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]pentoxy-(4R)-hydroxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc-methanol (9:1).

EXAMPLE 7

Solution of 6-(4-fluorophenyl)-2-methyl-4-pyridinol of formula I (1000 mg, 4.90 mmol), 1,3-dibromopropane (2475 mg, 12.25 mmol) and $K_2CO_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure3-bromopropyl-6-(4-fluorophenyl)-2-methyl-4-pyrimidyl ether of formula II.

Solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and $K_2CO_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave pure (4R)-hydroxy-(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal of formula IV.

To a stirred solution of (4R)-hydroxy-(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal of formula IV (660 mg, 1.00 mmol) in dichloromethane (10 mL) triethylamine (125 mg, 1.20 mmol) was added under N2 atmosphere at 0° C. After stirring for 5 min. acetylchloride (100 mg, 1.20 mmol) was added drop wise at same temperature and reaction mixture was allowed to stir at room temperature and reaction mixture was allowed to stir at room temperature for overnight and then poured into water, extracted with dichloromethane and dried over $Na_2SO_4$ and evaporated in vacuo to afforded the corresponding compound (4R)-acetyloxy-(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal.

(4R)-acetyloxy-(2S)-N-[{4-[6'-(4"-fluorophenyl)-2'-methylpyrimidine-4'-yloxy]propoxy}-5-methoxy-2-nitrobenzoyl]pyrrolidine-2-carboxaldehyde diethyl thioacetal (600 mg, 0.81 mmol) was dissolved in methanol (10 mL) and added $SnCl_2.2H_2O$ (880 mg 3.90 mmol) was refluxed for 1.5 h. Reaction mixture was then carefully adjusted to pH 8 with saturated $NaHCO_3$ solution and then extracted with ethyl acetate (3×30 mL). Combined organic phase was dried over $Na_2SO_4$ and evaporated under vacuum to afford the crude (4R)-acetyloxy-(2S)-N-[{4-[6'-(4"-fluorophenyl)-2'-methylpyrimidine-4'-yloxy]propoxy}-5-methoxy-2-aminobenzoyl]pyrrolidine-2-carboxaldehyde diethyl thioacetal of formula V.

Solution of formula V (350 mg, 0.50 mmol), $HgCl_2$ (300 mg, 1.10 mmol) and $CaCO_3$ (120 mg, 1.20 mmol) in $CH_3CN/H_2O$ (3:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]propoxy-(4R)-acetyloxy-(11aS)-1,2,3,11a-tetrahydro-5H-pyrrolo[2,1,c][1,4] benzodiazepin-5-one of formula VI, which was further purified by column chromatography on silica gel eluting first with ethyl acetate to remove traces of mercuric salts and further eluted with EtOAc-methanol (9:1).

EXAMPLE 8

Solution of 6-(4-fluorophenyl)-2-methyl-4-pyridinol of formula I (1000 mg, 4.90 mmol), 1,3-dibromopropane (2475 mg, 12.25 mmol) and $K_2CO_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II.

Solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and $K_2CO_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave pure (4R)-hydroxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal of formula IV.

To a stirred solution of (4R)-hydroxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal of formula IV (674 mg, 1.00 mmol) in dichloromethane (10 mL) triethylamine (125 mg, 1.2 mmol) was added under N2 atmosphere at 0° C. After stirring for 5 min. acetylchloride (100 mg, 1.20 mmol) was added drop wise at same temperature and reaction mixture was allowed to stir at room temperature for overnight and then poured into water, extracted with dichloromethane and dried over $Na_2SO_4$ and evaporated in vacuum to afforded the corresponding compound (4R)-acetyloxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal.

(4R)-acetyloxy-(2S)-N-[{4-[6'-(4"-fluorophenyl)-2'-methylpyrimidine-4'-yloxy]butoxy}-5-methoxy-2-nitrobenzoyl]pyrrolidine-2-carboxaldehyde diethyl thioacetal (600 mg, 0.79 mmol) was dissolved in methanol (10 mL) and added $SnCl_2.2H_2O$ (880 mg, 3.95 mmol) was refluxed for 1.5 h. The reaction mixture was then carefully adjusted to pH 8 with saturated $NaHCO_3$ solution and then extracted with ethyl acetate (3×30 mL). Combined organic phase was dried over $Na_2SO_4$ and evaporated under vacuum to afford crude (4R)-acetyloxy-(2S)-N-[{4-[6'-(4"-fluorophenyl)-2'-methylpyrimidine-4'-yloxy]butoxy}-5-methoxy-2-aminobenzoyl]pyrrolidine-2-carboxaldehyde diethyl thioacetal of formula V.

Solution of formula V (360 mg, 0.50 mmol), $HgCl_2$ (300 mg, 1.10 mmol) and $CaCO_3$ (120 mg, 1.20 mmol) in $CH_3CN/H_2O$ (3:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]butoxy-(4R)-acetyloxy-(11aS)-1,2,3,11a-tetrahydro-5H-pyrrolo[2,1,c][1,4]benzodiazepin-5-one of formula VI, which was further purified by column chromatography on silica gel eluting first with ethyl acetate to remove traces of mercuric salts and further eluted with EtOAc-methanol (9:1).

EXAMPLE 9

Solution of 6-(4-fluorophenyl)-2-methyl-4-pyridinol of formula I (1000 mg, 4.90 mmol), 1,3-dibromopropane (2475 mg, 12.25 mmol) and $K_2CO_3$ (2030 mg, 14.70 mmol) in dry acetone (40 mL) was refluxed for 48 h. After the completion of reaction as indicated by TLC, EtOAc-hexane (2:8), the reaction mixture was poured on to the water and then extracted with ethyl acetate. Evaporation of the organic layer gave the crude product, which was further purified by column chromatography on silica gel eluting with EtOAc-hexane (5:95) gave the pure 3-bromopropyl-6-(4-fluorophenyl)-2-methyl-4-pyrimidyl ether of formula II.

A solution of 3-bromopropyl-6-(4-fluorophenyl)-2-methyl-4-pyrimidyl ether of formula II (1200 mg, 3.69 mmol), A solution of (4R)-hydroxy-(2S)-N-(4-hydroxy-5-methoxy-2-nitrobenzoyl)pyrrolidine-2-carboxaldehyde diethylthioacetal of formula III (1472 mg, 3.69 mmol) and $K_2CO_3$ (1530 mg, 11.07 mmol) in dry acetone (20 mL) was refluxed for 48 h. After the completion of reaction as indicated by TLC, EtOAc, the reaction mixture was poured on to the water and then extracted with ethyl acetate. Evaporation of the organic layer gave the crude product, which was further purified by column chromatography on silica gel eluting with EtOAc-hexane (1:3) gave pure (4R)-hydroxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula IV.

To a stirred solution of (4R)-hydroxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal of formula IV (688 mg, 10 mmol) in dichloromethane (10 mL) triethylamine (125 mg, 1.20 mmol) was added under $N_2$ atmosphere at 0° C. After stirring for 5 min. acetylchloride (100 mg, 1.20 mmol) was added drop wise at same temperature and reaction mixture was allowed to stir at room temperature overnight and then poured into water, extracted with dichloromethane and dried over Na₂SO₄ and evaporated in vacuum to afforded the corresponding compound (4R)-acetyloxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal.

(4R)-acetyloxy-(2S)-N-[{4-[6'-(4"-fluorophenyl)-2'-methylpyrimidine-4'-yloxy]pentoxy}-5-methoxy-2-nitrobenzoyl]pyrrolidine-2-carboxaldehyde diethyl thioacetal (600 mg, 0.78 mmol) was dissolved in methanol (10 mL) and added SnCl₂.2H₂O (880 mg 3.90 mmol) was refluxed for 1.5 h. The reaction mixture was then carefully adjusted to pH 8 with saturated NaHCO₃ solution and then extracted with ethyl acetate (3×30 mL). Combined organic phase was dried over Na₂SO₄ and evaporated under vacuum to afford crude (4R)-acetyloxy-(2S)-N-[{4-[6'-(4"-fluorophenyl)-2'-methylpyrimidine-4'-yloxy]pentoxy}-5-methoxy-2-aminobenzoyl]pyrrolidine-2-carboxaldehyde diethyl thioacetal of formula V.

Solution of formula V (365 mg, 0.50 mmol), HgCl₂ (300 mg, 1.10 mmol) and CaCO₃ (120 mg, 1.20 mmol) in CH₃CN/H₂O (3:1, 15 mL) was stirred at room temperature for 12 h until TLC (EtOAc), indicates complete loss of starting material. Then organic layer is evaporated in vacuum and the residue is diluted with EtOAc. To this saturated NaHCO₃ was added slowly at room temperature and the mixture is filtered through celite and washed with ethyl acetate. The filtrate is evaporated in vacuum to get crude 7-methoxy-8-[6'-(4"-fluorophenyl)-2'-methylpyrimidine-4'-yloxy]pentoxy-(4R)-acetyloxy-(11aS)-1,2,3,11a-tetrahydro-5H-pyrrolo[2,1-c][1,4]benzodiazepin-5-one of formula VI, which was further purified by column chromatography on silica gel eluting first with ethyl acetate to remove traces of mercuric salts and further eluted with EtOAc-methanol (9:1).

Biological Activity: In vitro biological activity studies were carried out at National Cancer Institute (USA).

Cytotoxicity: Compounds VIa and VIb were evaluated in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$TGI and $\log_{10}$LC50 as well as $\log_{10}$GI50 for VIa and VIb are listed in Table 1. As demonstrated by mean graph pattern, compound VIb exhibits an interesting profile of activity and selectivity for various cell lines. The mean graph mid point of $\log_{10}$TGI and $\log_{10}$LC50 showed similar pattern to the $\log_{10}$GI50 mean graph mid points.

TABLE 1

$\log_{10}$ GI50 $\log_{10}$ TGI and $\log_{10}$ LC50 mean graphs midpoints (MG_MID) of in vitro cytotoxicity data for the compounds VIa and VIb against human tumour cell lines.

| Compound | $\text{Log}_{10}$ GI50 | $\text{Log}_{10}$ TGI | $\text{Log}_{10}$ LC50 |
|---|---|---|---|
| VIa | −4.73 | −4.34 | −4.10 |
| VIb | −6.41 | −5.57 | −4.69 |

The comparison of the data of Table 2 reveals the importance of the alkane spacer. As the alkane spacer increased from 3–4 the cytotoxic activity has moderately enhanced. The 4 carbon spacer of compound VIb confers a suitable fit in the minor groove of double helix DNA and shows slightly higher activity in this series of compounds VIa and VIb.

| Cancer | Compound VIa | Compound VIb |
|---|---|---|
| Leukaemia | −4.03 | −5.41 |
| non-small-cell lung | −4.07 | −4.61 |
| Colon | −4.12 | −4.67 |
| CNS | −4.10 | −4.40 |
| Melanoma | −4.14 | −5.22 |
| Ovarian | −4.05 | −4.33 |
| Renal | −4.18 | −4.39 |
| Prostate | −4.00 | −4.45 |
| Breast | −4.09 | −4.52 |

Each cancer type represents the average of six to eight different cancer cell lines.

We claim:

1. A compound of formula VI wherein R is H, OH, or OAc and n is 3 to 5:

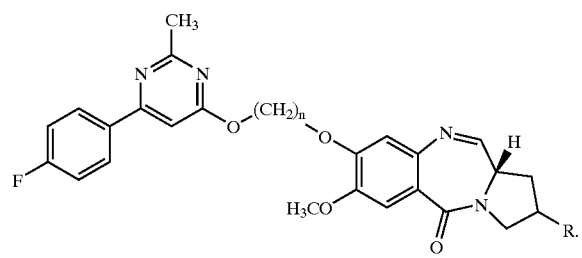

2. The compound as claimed in claim 1 of the structural formula shown below:

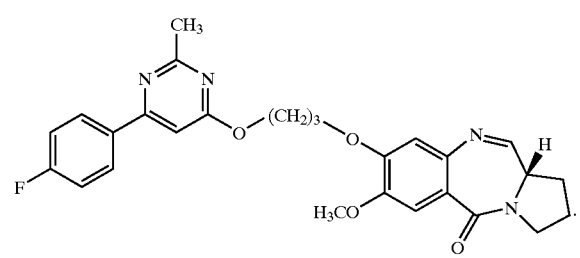

3. The compound as claimed in claim 1 of the structural formula shown below:

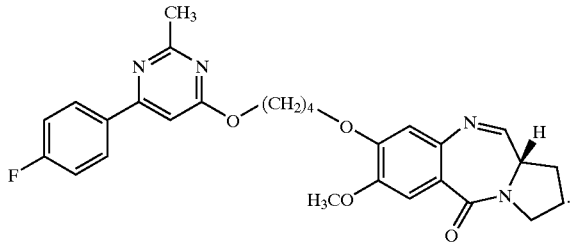

4. The compound as claimed in claim 1 of the structural formula shown below:

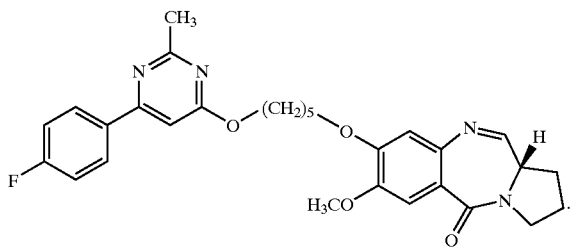

5. The compound as claimed in claim 1 of the structural formula shown below:

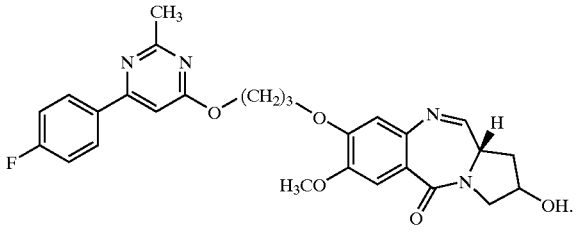

6. The compound as claimed in claim 1 of the structural formula shown below:

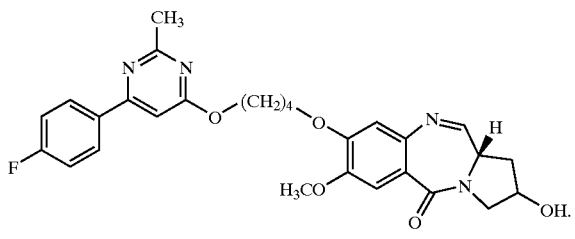

7. The compound as claimed in claim 1 of the structural formula shown below:

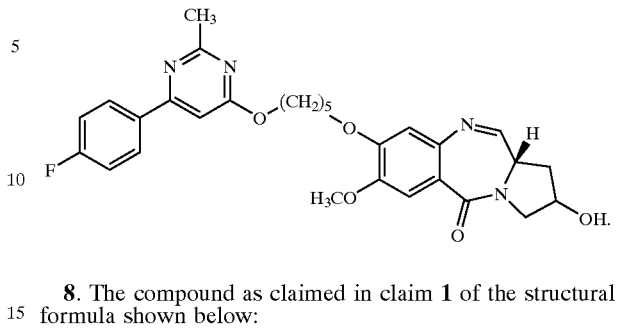

8. The compound as claimed in claim 1 of the structural formula shown below:

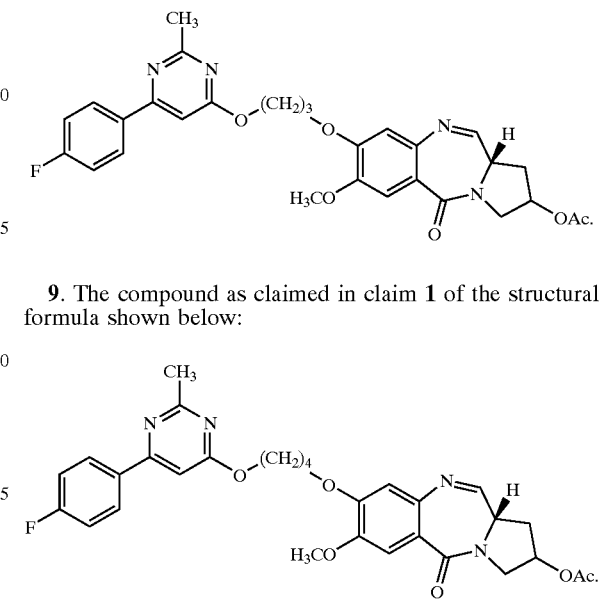

9. The compound as claimed in claim 1 of the structural formula shown below:

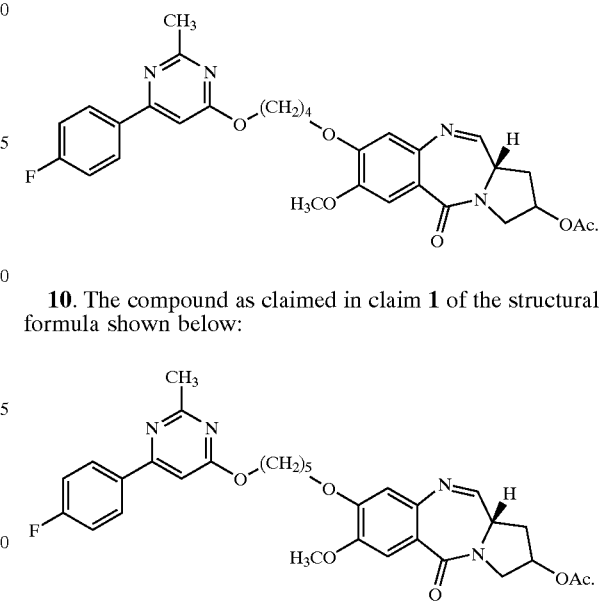

10. The compound as claimed in claim 1 of the structural formula shown below:

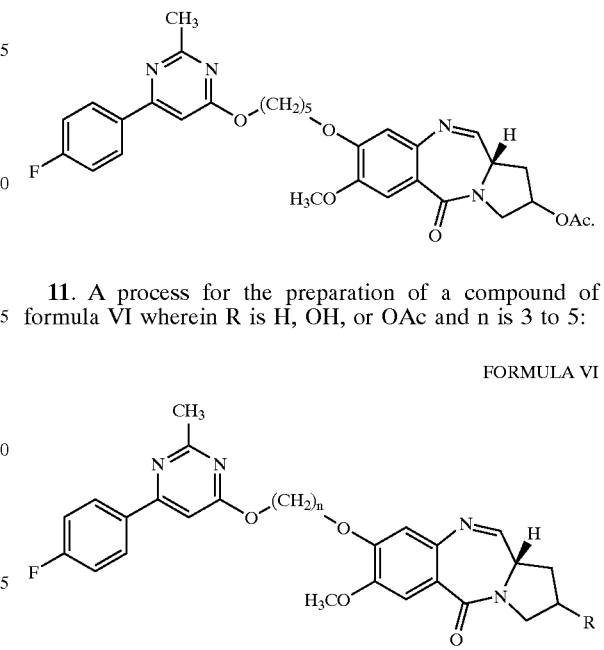

11. A process for the preparation of a compound of formula VI wherein R is H, OH, or OAc and n is 3 to 5:

FORMULA VI

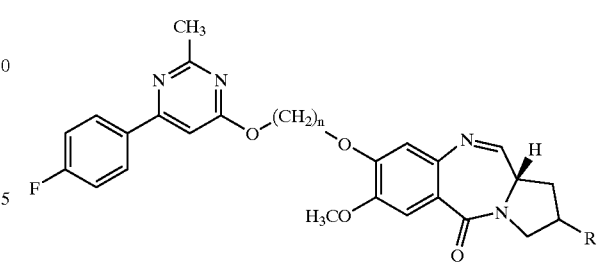

the process comprising reacting 6-4-(4-fluorophenyl)-2-methyl-4-pyrimidinol of formula I

FORMULA I

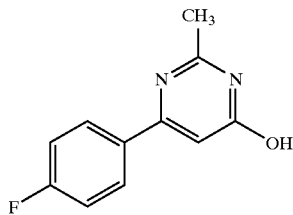

with a dibromoalkane in an aprotic water miscible organic solvent in the presence of a mild inorganic base up to refluxing temperature for a period up to 48 h, isolating n-bromoalkyl-6-(4-fluorophenyl)-2-methyl-4-pyrimidinyl ether of formula II with (2S)-N-(4-hydroxy-5-methoxy-2-nitrobenzoyl)pyrrolidine-2-carboxaldehyde diethyl thioacetal of formula III

II

III

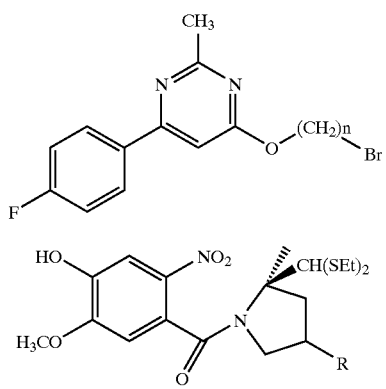

in the presence of a mild inorganic base in the presence of aprotic water miscible organic solvent up to refluxing for a period of 48 h, isolating (2S)-N-[{4-[6"-(4'-fluorophenyl)-2'-methylpyrimidine-4'-yloxy]alkoxy}-5-methoxy-2-nitrobenzoyl]pyrrolidine-2-carboxaldehyde diethyl thioacetal of formula IV where n is 3 to 5,

IV

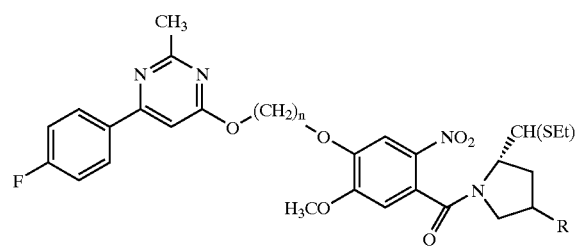

reducing the compound of formula IV with $SnCl_2.2H_2O$ in presence of organic solvent up to a reflux temperature, isolating (2S)-N-[{4-[6'-(4"-fluorophenyl)-2'-methylpyrimidine-4'-yloxy]alkoxy}-5-methoxy-2-aminobenzoyl]pyrrolidine-2-carboxaldehyde diethyl thioacetal of formula V where n is 3 to 5,

V

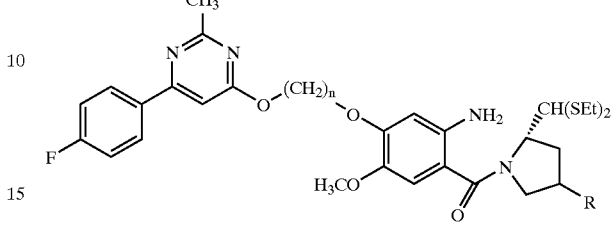

reacting the compound of formula V with a deprotecting agent to obtain a pyrrolo[2,1-c][1,4]benzodiazepine of formula VI.

12. The process as claimed in claim 11 wherein the aprotic water miscible organic solvent is selected from the group consisting of acetone, THF and DMF.

13. The process as claimed 11 wherein the mild inorganic base is selected from the group consisting of $K_2CO_3$, $CsCO_3$ and $BaCO_3$.

14. The process as claimed in claim 11 wherein the isolated (2S)-N-[{4-[6'-(4"-fluorophenyl)-2'-methylpyrimidine-4'-yloxy]alkoxy}-5-methoxy-2-nitrobenzoyl]pyrrolidine-2-carboxaldehyde diethyl thioacetal of formula IV is reduced using $SnCO_2.2H_2O$ in the presence of an organic solvent.

15. A method for the treatment of cancer in a subject suffering therefrom comprising administering a pharmaceutically effective dose of a compound of formula VI wherein R is H, OH, or OAc and n is 3 to 5:

FORMULA VI

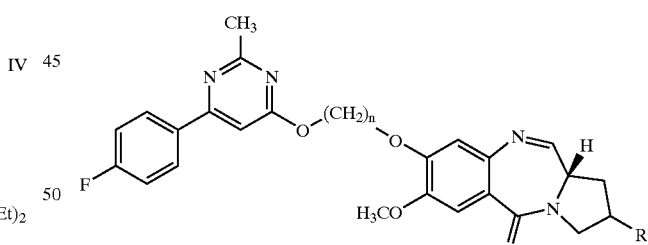

wherein the cancer is leukemia, non-small-cell lung, colon, CNS, melanoma, ovarian, prostate or breast cancer.

* * * * *